United States Patent [19]

Sayo et al.

[11] Patent Number: 4,933,482

[45] Date of Patent: Jun. 12, 1990

[54] PROCESS FOR PREPARING OPTICALLY ACTIVE ALCOHOL

[75] Inventors: Noboru Sayo; Takao Saito; Hidenori Kumobayashi; Susumu Akutagawa, all of Kanagawa; Ryoji Noyori; Hidemasa Takaya, both of Aichi, all of Japan

[73] Assignee: Takasago International Corporation, Tokyo, Japan

[21] Appl. No.: 204,480

[22] Filed: Jun. 9, 1988

[30] Foreign Application Priority Data

Jun. 11, 1987 [JP] Japan .................................. 62-145975

[51] Int. Cl.$^5$ ..................... C07C 103/16; C07C 69/66; C07C 69/76; C07C 69/74
[52] U.S. Cl. ..................................... 558/252; 564/201; 560/179; 560/60; 560/126; 560/184
[58] Field of Search ................... 564/201; 560/179, 60, 560/126, 184; 558/252

[56] References Cited

U.S. PATENT DOCUMENTS 4,273,933 6/1981 Harada et al. ....................... 560/179

OTHER PUBLICATIONS

Chemical Abstracts, vol. 83, No. 13, Sep. 28, 1975 (Solodar), Entitled: "Asymmetric Hydrogenation of Ketones", p. 488, col. 2, No. 113 607k.
Chemical Abstracts, vol. 94, No. 15, Apr. 13, 1981, (Tai), Entitled: "Assymmetrically Modified Nickel-catalyst and Its Use of Optically Active 3-Hydroxy Acids", p. 631, column 1, No. 129 759s.
Title: "Asymmetric Hydrogenation of Ketones"; Chemtech Jul. 1975; pp. 421–423; Author–John Solodar.
Title: "Asymmetrically Modified Nickel Catalyst Its Application to the Preparation of Optically Active 3-Hydroxyacid", by Akira Tai, pp. 44–53, (1980), Yukagaku.

Primary Examiner—Mary C. Lee
Assistant Examiner—Robert C. Whittenbaugh
Attorney, Agent, or Firm—Sughrue, Mion, Zinn, Macpeak & Seas

[57] ABSTRACT

A process for preparing an optically active alcohol is disclosed, which comprises asymmetrically hydrogenating a β-keto acid derivative in the presence of a ruthenium-optically active phosphine complex as a catalyst. The resulting alcohol has high optical purity.

2 Claims, No Drawings

PROCESS FOR PREPARING OPTICALLY ACTIVE ALCOHOL

FIELD OF THE INVENTION

This invention relates to a process for preparing an optically active alcohol useful as an intermediate for synthesizing pharmaceuticals, liquid crystal material, and the like by the asymmetric hydrogenation of a β-keto acid derivative in the presence of a ruthenium-optically active phosphine complex as a catalyst.

BACKGROUND OF THE INVENTION

Known techniques for asymmetrically synthesizing optically active alcohols include a process comprising asymmetric hydrogenation using baker's yeast and a process comprising asymmetric hydrogenation using a specific catalyst.

In particular, with respect to asymmetric hydrogenation of an l-keto acid derivative to obtain optically active alcohols, it has been reported that the asymmetric hydrogenation can be carried out by using a rhodium-optically active phosphine complex as a catalyst. For example, J. Solodar reports in Chemtech., 421–423 (1975) that asymmetric hydrogenation of methyl acetoacetate gives methyl 3-hydroxybutyrate in an optical yield of 71% ee.

Further, asymmetric hydrogenation using a tartaric acid-modified nickel catalyst has been proposed. According to this technique, asymmetric hydrogenation of methyl acetoacetate gives methyl 3-hydroxybutyrate in an optical yield of 85% ee as disclosed in Tai, Yukagaku, 822–831 (1980).

Although the process using baker's yeast produces an alcohol having relatively high optical purity, the resulting optically active alcohol is limited in absolute configuration, and synthesis of an enantiomer is difficult.

The process utilizing asymmetric hydrogenation of a β-keto acid derivative in the presence of a rhodium-optically active phosphine complex does not produce an alcohol having sufficient optical purity. Besides, metallic rhodium to be used in the catalyst is expensive due to limitations in place and quantity of production. When used as a catalyst component, it forms a large proportion in cost of the catalyst, ultimately resulting in increase in cost of the final commercial products.

The process using a tartaric acid-modified nickel catalyst involves disadvantages of difficulty in preparing the catalyst and insufficient optical yield.

SUMMARY OF THE INVENTION

As a result of extensive investigations with the purpose of settling the above-described problems, the inventors have found that an optically active alcohol having high optical purity can be obtained by asymmetric hydrogenation of a β-keto acid derivative in the presence of a relatively cheap ruthenium-optically active phosphine complex as a catalyst. The present invention has been completed based on this finding.

The present invention relates to a process for preparing an optically active alcohol represented by formula (I):

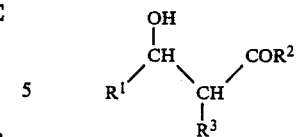

wherein $R^1$ represents a substituted or unsubstituted lower alkyl group, a trifluoromethyl group or an aryl group; $R^2$ represents $OR^4$, wherein $R^4$ represents an alkyl group having from 1 to 8 carbon atoms, $SR^5$, wherein $R^5$ represents a lower alkyl group or a phenyl group, or $NR^6R^7$, wherein $R^6$ and $R^7$, which may be the same or different, each represents a hydrogen atom, a lower alkyl group or a benzyl group; and $R^3$ represents a hydrogen atom, a halogen atom, a lower alkyl group, a lower alkoxycarbonyl group or a lower alkoxycarbonyl-lower alkyl group; or $R^1$ and $R^3$ are connected to each other to form a methylene chain, forming a 4- to 6-membered ring together with the carbon atoms therebetween, which comprises asymmetrically hydrogenating a β-keto acid derivative represented by formula (II):

wherein $R^1$, $R^2$, and $R^3$ are as defined above, in the presence of a ruthenium-optically active phosphine complex as a catalyst.

DETAILED DESCRIPTION OF THE INVENTION

In formulae (I) and (II), substituents for the lower alkyl group as represented by $R^1$ include a halogen atom, a hydroxyl group, an amino group, a lower alkyl-substituted amino group, a benzyloxy group, and an aryl group.

The β-keto acid derivative represented by formula (II) which can be used in the present invention as a starting compound specifically includes methyl acetoacetate, ethyl acetoacetate, isopropyl acetoacetate, n-butyl acetoacetate, t-butyl acetoacetate, n-pentyl acetoacetate, n-hexyl acetoacetate, n-heptyl acetoacetate, n-octyl acetoacetate, methyl 4-chloroacetoacetate, ethyl 4-chloroacetoacetate, methyl 4-fluoroacetoacetate, methyl 3-oxopentanoate, methyl 3-oxohexanoate, methyl 3-oxoheptanoate, ethyl 3-oxooctanoate, ethyl 3-oxononanoate, ethyl 3-oxodecanoate, ethyl 3-oxoundecanoate, ethyl 3-oxo-3-phenylpropanoate, ethyl 3-oxo-3-p-methoxyphenylpropanoate, ethyl 4-phenyl-3-oxobutanoate, methyl 5-phenyl-3-oxopentanoate ethyl 3-trifluoromethyl-3-oxopropanoate, ethyl 4-hydroxy-3-oxobutanoate, methyl 4-benzyloxy-3-oxobutanoate, ethyl 4-benzyloxy-3-oxobutanoate, methyl 4-amino-3-oxobutanoate, ethyl 4-methylamino-3-oxobutanoate, ethyl 4-dimethylamino-3-oxobutanoate, ethyl 4-dimethylamino-3-oxobutanoate, ethyl 2-methylacetoacetate, ethyl 2-chloroacetoacetate, diethyl 2-acetylsuccinate, diethyl 2-acetylglutalate, 2-carboethoxy-cyclopentanone, 2-carboethoxy-cyclohexanone, dimethyl acetylmalonate, 3-oxobutanoic dimethylamide, 3-oxobutanoic benzylamide, methyl 3-oxobutanethioate, ethyl 3oxobutanethioate, phenyl 3-oxobutanethioate, etc.

The ruthenium-optically active phosphine complex to be used as a catalyst include those represented by the following formulae (III) and (V):

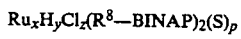

$$Ru_xH_yCl_z(R^8\text{-BINAP})_2(S)_p \quad (III)$$

wherein $R^8$-BINAP represents a tertiary phosphine represented by the formula (IV):

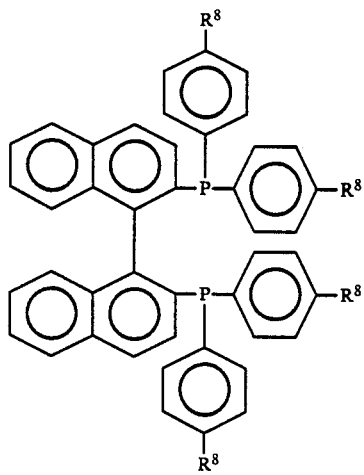

(IV)

wherein $R^8$ represents a hydrogen atom, a methyl group or a t-butyl group; S represents a tertiary amine; when y represents 0, then x represents 2, z represents 4, and p represents 1; and when y represents 1, then x represents 1, z represents 1, and p represents 0.

$$[RuH_l(R^8\text{-BINAP})_v]Y_w \quad (V)$$

wherein $R^8$-BINAP is as defined above; Y represents $ClO_4$, $BF_4$ or $PF_6$; when l represents 0, then v represents 1, and w represents 2; and when l represents 1, then v represents 2, and w represents 1.

In formulae (III) and (V), "BINAP" represents a 2,2-bis(diphenylphosphino)-1,1'-binaphthyl moiety (hereinafter the same).

The compound of formula (III) can be obtained by the process disclosed in T. Ikariya et al., *J. Chem. Soc., Chem. Commun.*, 922-924 (1985) and Japanese Patent Application (OPI) No. 63690/86 (the term "OPI" as used herein means "unexamined published Japanese patent application"). More specifically, the complex of formula (III) wherein y is 0 can be prepared by reacting 1 mol of $[RuCl_2(COD)]_n$ (wherein COD represents cycloocta-1,5-diene, hereinafter the same), which is obtainable by reacting ruthenium chloride and COD in an ethanol solution, and 1.2 mols of a 2,2'-bis(di-p-$R^8$-phenylphosphino)-1,1'-binaphthyl ($R^8$-BINAP) in a solvent, e.g., toluene, ethanol, etc., in the presence of 4 mols of a tertiary amine, e.g., triethylamine. The complex of formula (III) wherein y is 1 can be obtained by reacting 1 mol of $[RuCl_2(COD)]_n$, 2.25 mols of $R^8$-BINAP, and 4.5 mols of a tertiary amine.

The complex of formula (V) wherein l is 0, v is 1, and w is 2 can be prepared by reacting $Ru_2Cl_4(R^8BINAP)_2$·(NEt$_3$) (wherein Et represents an ethyl group, hereinafter the same), which is obtained by the abovedescribed process, with a salt represented by formula (VI):

$$MY \quad (VI)$$

wherein M represents Na, K, Li, Mg or Ag; and Y is as defined above, in a solvent system comprising water and methylene chloride in the presence of a quaternary ammonium salt or quaternary phosphonium salt represented by formula (VII):

$$R^9R^{10}R^{11}R^{12}AB \quad (VII)$$

wherein $R^9$, $R^{10}$, $R^{11}$, and $R^{12}$ each represents an alkyl group having from 1 to 16 carbon atoms, a phenyl group or a benzyl group; A represents a nitrogen atom or a phosphorus atom; and B represents a halogen atom, as a phase transfer catalyst. The reaction can be carried out by adding the reactants and the phase transfer catalyst of formula (VII) to a mixed solvent of water and methylene chloride and stirring the system. The amounts of the salt of formula (VI) and the phase transfer catalyst of formula (VII) to be added range from 2 to 10 mols, and preferably 5 mols, and from 1/100 to 1/10 mol, respectively, per mol of ruthenium. The reaction sufficiently proceeds by stirring at a temperature of from 5° to 30° C. for a period of from 6 to 18 hours, and usually 12 hours. Examples of the phase transfer catalyst of formula (VII) are described in literature, i.e., W. P. Weber and G. W. Gokel, Sokan Ido Shokubai (Japanese translation), 1st Ed., Kagaku Dojinsha (1978). After completion of the reaction, the reaction mixture is allowed to stand still, followed by liquid separation. After the aqueous layer is removed, the methylene chloride solution is washed with water, and methylene chloride is removed by distillation under reduced pressure to obtain the desired compound.

The complex of formula (V) where l is 1, v is 2, and w is 1 can be prepared by reacting $RuHCl(R^8BINAP)_2$ obtainable by the process disclosed in Japanese Patent Application (OPI) No. 63690/86 with the salt of formula (VI) in a mixed solvent of water and an organic solvent, e.g., methylene chloride, in the presence of the phase transfer catalyst of formula (VII). The amounts of the salt of formula (VI) and the phase transfer catalyst of formula (VII) range from 2 to 10 mols, and preferably 5 mols, and from 1/100 to 1/10 mol, respectively, per mol of ruthenium. This reaction sufficiently proceeds by stirring at a temperature of from 5° to 30° C. for a period of from 6 to 18 hours, and usually 12 hours.

Specific examples of the above-described ruthenium-phosphine complex according to the present invention are shown below.

$Ru_2Cl_4(BINAP)_2(NEt_3)$
$Ru_2Cl_4(T\text{-BINAP})_2(NEt_3)$
    [T-BINAP represents 2,2'-bis(di-p-tolylphosphino)-1,1'-binaphthyl]
$Ru_2Cl_4(T\text{-Bu-BINAP})_2(NEt_3)$
    [t-Bu-BINAP represents 2,2'-bis(di-p-t-butylphenylphosphino)-1,1'-binaphthyl]
RuHCl[BINAP]$_2$
RuHCl[T-BINAP]$_2$
RuHCl[t-Bu-BINAP]$_2$
[Ru(BINAP)](ClO$_4$)$_2$
[Ru(T-BINAP)](ClO$_4$)$_2$
[Ru(t-Bu-BINAP)](ClO$_4$)$_2$
[Ru(BINAP)](BF$_4$)$_2$
[Ru(T-BINAP)](BF$_4$)$_2$
[Ru(t-Bu-BINAP)](BF$_4$)$_2$
[Ru(BINAP)](PF$_6$)$_2$
[Ru(T-BINAP)](PF$_6$)$_2$

[RuH(BINAP)₂]ClO₄
[RuH(T-BINAP)₂]ClO₄
[RuH(BINAP)₂]BF₄
[RuH(T-BINAP)₂]BF₄
[RuH(BINAP)₂]PF₆
[RuH(T-BINAP)₂]PF₆

In carrying out the present invention, a β-keto acid derivative of formula (II) is dissolved in an amphiprotic solvent, e.g., methanol, ethanol, methyl cellosolve, etc., or a mixed solvent of such an amphiprotic solvent with tetrahydrofuran, toluene, benzene, methylene chloride, etc. The solution is charged in an autoclave, and from 1/100 to 1/50,000 mol of a ruthenium-optically active phosphine complex is added thereto per mol of the β-keto acid derivative. The hydrogenation reaction is effected under stirring at a temperature of from 5° to 50° C., and preferably from 25° to 35° C., at a hydrogen pressure of from 5 to 100 kg/cm² for a period of from 1 to 48 hours. After completion of the reaction, the solvent is removed by distillation, and the residue is distilled under reduced pressure or subjected to silica gel column chromatography to thereby isolate the desired optically active alcohol of formula (I) in a substantially quantitative yield.

The present invention will now be illustrated in greater detail with reference to Reference Examples and Examples, but it should be understood that the present invention is not deemed to be limited thereto. In these examples, analytical instruments and conditions used for various analyses are as follows.

(1) Gas Chromatography (GC)

SHIMADZU GC-9A manufactured by Shimadzu Corporation
  Column: PEG-20M Silica Capillary, 0.25 mm in diameter and 25 m in length, manufactured by Gasukuro Kogyo Inc.
  Measurement Temperature: 100°–250° C. and increasing at a rate of 3° C./min.

(2) High Performance Liquid Chromatography (HPLC): Hitachi Liquid Chromatography-655A-11 manufactured by Hitachi, Ltd.
  Column: Chemcopack Nucleosil 100-3, 4.6 mm in diameter and 300 mm in length, manufactured by Chemco Co.
  Developing Solvent: Hexane:diethyl ether=7:3; flow rate: 1 ml/min
  Detector: UV Detector 655A (UV-254), manufactured by Hitachi, Ltd.

(3) Optical Rotation:
  Polarimeter DIP-4, manufactured by Nippon Bunko Kogyo K.K.

(4) 31P NMR Spectrum:
  JNM-GX400 (161 MHz) manufactured by JEOL Ltd. Chemical shift was determined by using 85% phosphoric acid as an external standard.

REFERENCE EXAMPLE 1

Synthesis of Ru₂Cl₄[(+)-BINAP]₂(NEt3) (di[2,2′-bis(di-phenylphosphino)-1,1′-binaphthyl]tetrachloro-diruthenium triethylamine):

To 100 ml of toluene were added 1 g (3.56 mmol) of [RuCl₂(COD)]ₙ, 2.66 g (4.27 mmol) of (+)-BINAP, and 1.5 g of triethylamine in a nitrogen atmosphere, and the mixture was heat-refluxed for 10 hours. The solvent was removed from the reaction mixture by distillation under reduced pressure, and the residual solid was dissolved in methylene chloride, followed by filtration through Celite. The filtrate was concentrated to dryness to obtain 3.7 g of the entitled compound as a deep brown solid.

Elemental Analysis for C₉₄H₇₉Cl₄NP₄Ru₂: Calcd. (%): Ru 11.96; C 66.85; H 4.71; P 7.33 Found (%): Ru 11.68; C 67.62; H 4.97; P 6.94

31P NMR (CDCl₃) ppm: 51.06 (s), 51.98 (s), 53.87 (s), and 54.83 (s)

REFERENCE EXAMPLE 2

Synthesis of [Ru((−)-T-BINAP)](Cl₄)₂([2,2′-bis(di-p-tolylphosphino)-1,1′-binaphthyl]ruthenium perchlorate):

In a 250 ml-volume Schlenk's tube was charged 0.54 g (0.3 mmol) of Ru₂Cl₄[(−)-T-BINAP]2(NEt3). After thorough displacement of the atmosphere with nitrogen gas, 60 ml of methylene chloride was added thereto, and then a solution of 0.73 g (6.0 mmols) of sodium perchlorate in 60 ml of water and a solution of 16 mg (0.06 mmol) of triethylbenzylammonium bromide in 3 ml of water were added to the mixture. The mixture was stirred at room temperature for 12 hours. After completion of the reaction, the reaction mixture was allowed to stand, and the aqueous layer was removed. The methylene chloride was removed from the organic layer by distillation under reduced pressure, and the residue was dried under reduced pressure to obtain 0.59 g (yield: 99.6%) of the entitled compound as a deep brown solid.

Elemental Analysis for C₄₈H₄₀Cl₂O₈P₂Ru: Calcd. (%): Ru 10.32; C 58.90; H 4.12; P 6.33. Found (%): Ru 10.08; C 58.61; H 4.53; P 5.9.

31P NMR (CDCl₃) ppm: 12.920 (d, J=41.1 Hz) and 61.402 (d, J=41.1 Hz)

EXAMPLE 1

Synthesis of Methyl (3R)-(-)-3-Hydroxybutyrate

In a 200 ml-volume stainless steel-made autoclave whose atmosphere had been replaced with nitrogen were charged 10 ml (93 mmols) of methyl acetoacetate, 50 ml of methanol, and 0.5 ml of water, and 42 mg (0.025 mmol) of Ru₂Cl₄((+)-BINAP)₂(NEt3) as prepared in Reference Example 1 was added thereto to effect hydrogenation at a temperature of 30° C. under a hydrogen pressure of 40 kg/cm² for 20 hours. The solvent was removed by distillation, and the residue was distilled under reduced pressure to obtain 10.8 g (98%) of the entitled compound having a boiling point of 72° C./17 mmHg.

The product was found to have a purity of 99.0% by GC and an optical rotation [α]$_D^{20}$ of −24.17° (neat).

Thirty milligrams of the resulting alcohol was esterified with (+)-α-methoxy-α-trifluoromethylphenylacetyl chloride, and the ester was analyzed by GC and HPLC. The results revealed that the product was a mixture comprising 99.55% of methyl (3R)-(−)-3-hydroxybutyrate and 0.45% of methyl (3S)-(+)-3-hydroxybutyrate. Accordingly, the optical yield of the methyl (3R)-(−)-3-hydroxybutyrate was found to be 99.1%.

EXAMPLES 2 TO 17

The same procedure of Example 1 was repeated, except for altering the reaction substrate, catalyst and reaction conditions as shown Table 1 below. The analytical results obtained are shown in Table 2.

In Examples 7, 8, 14, and 15, the optically active alcohol produced contains two asymmetric centers forming diastereomers. A ratio of the syn form to the anti form in each case was determined by HPLC, and the optical yield of each form was determined. The results obtained are separately shown in Table 3.

TABLE 1

Substrate:

$$R^1-\underset{\underset{R^3}{|}}{C}(=O)-CH-COR^2$$

| Example No. | $R^1$ | $R^2$ | $R^3$ | Catalyst | Substrate/ Catalyst (mol/mol) | Hydrogen Pressure (kg/cm²) | Temperature (°C.) | Time (hr) |
|---|---|---|---|---|---|---|---|---|
| 2 | CH₃ | OC₂H₅ | H | Ru₂Cl₄[(+)-BINAP]₂(NEt₃) | 2000 | 40 | 30 | 22 |
| 3 | CH₃ | OiPr | H | [Ru((−)-BINAP)](ClO₄)₂ | 1000 | 5 | 30 | 20 |
| 4 | CH₃ | OtBu | H | [Ru((−)-T-BINAP)](BF₄)₂ | 1000 | 5 | 30 | 20 |
| 5 | CH₃CH₂ | OCH₃ | H | Ru₂Cl₄[(+)-BINAP]₂(NEt₃) | 2000 | 40 | 30 | 18 |
| 6 | CH₃(CH₂)₃ | OCH₃ | H | Ru₂Cl₄[(+)-T-BINAP]₂(NEt₃) | 1000 | 40 | 30 | 18 |
| 7 | CH₃ | OC₂H₅ | Cl | [RuH((+)-BINAP)₂]ClO₄ | 1000 | 30 | 30 | 15 |
| 8 | CH₃ | OC₂H₅ | CH₃ | Ru₂Cl₄[(−)-T-BINAP]₂(NEt₃) | 1000 | 80 | 30 | 24 |
| 9 | CF₃ | OC₂H₅ | H | RuHCl[(+)-BINAP]₂ | 1000 | 80 | 30 | 16 |
| 10 | PhCH₂OCH₂ | OCH₃ | H | Ru₂Cl₄[(−)-T-BINAP]₂(NEt₃) | 1000 | 40 | 30 | 20 |
| 11 | CH₃ | NHCH₂Ph | H | [Ru((−)-T-BINAP)](PF₆)₂ | 1000 | 40 | 30 | 20 |
| 12 | (CH₃)₂NCH₂ | OC₂H₅ | H | Ru₂Cl₄[(+)-BINAP]₂(NEt₃) | 1000 | 40 | 30 | 18 |
| 13 | CH₃ | SC₂H₅ | H | [Ru((+)-T-BINAP)](ClO₄)₂ | 1000 | 40 | 30 | 30 |
| 14 | 2-(ethoxycarbonyl)cyclohexan-1-one | | | [Ru((+)-BINAP)](BF₄)₂ | 1000 | 40 | 30 | 24 |
| 15 | CH₃ | OCH₃ | CH₂CO₂CH₃ | RuHCl[(−)-T-BINAP]₂ | 1000 | 40 | 30 | 36 |
| 16 | ClCH₂ | CH₃ | H | Ru₂Cl₄[(+)-BINAP]₂(NEt₃) | 1000 | 100 | 30 | 16 |
| 17 | BrCH₂ | CH₃ | H | Ru₂Cl₄[(−)-BINAP]₂(NEt₃) | 1000 | 40 | 30 | 20 |

Note:
iPr represents an isopropyl group; tBu represents a t-butyl group; and Ph represents a phenyl group.

TABLE 2

| Example No. | Product | Yield (%) | Optical Yield (% ee) |
|---|---|---|---|
| 2 | 3-hydroxybutanoic acid ethyl ester (OH–CH(CH₃)–CH₂–CO–OC₂H₅) | 99 | 99.1 |
| 3 | 3-hydroxybutanoic acid isopropyl ester (OH–CH(CH₃)–CH₂–CO–OiPr) | 98 | 98.0 |
| 4 | 3-hydroxybutanoic acid t-butyl ester (OH–CH(CH₃)–CH₂–CO–OtBu) | 98 | 96.4 |
| 5 | 3-hydroxypentanoic acid methyl ester (OH–CH(C₂H₅)–CH₂–CO–OCH₃) | 99 | 99.3 |
| 6 | 3-hydroxyheptanoic acid methyl ester | 99 | 99.2 |
| 7 | 2-chloro-3-hydroxybutanoic acid ethyl ester | 95 | see Table 3 |
| 8 | 2-methyl-3-hydroxybutanoic acid ethyl ester | 97 | see Table 3 |
| 9 | 4,4,4-trifluoro-3-hydroxybutanoic acid ethyl ester (F₃C–CH(OH)–CH₂–CO–OC₂H₅) | 95 | 46 |
| 10 | 4-benzyloxy-3-hydroxybutanoic acid methyl ester (PhCH₂O–CH₂–CH(OH)–CH₂–CO–OCH₃) | 97 | 95 |
| 11 | 3-hydroxy-N-benzylbutanamide (OH–CH(CH₃)–CH₂–CO–NHCH₂Ph) | 94 | 88 |
| 12 | 4-dimethylamino-3-hydroxybutanoic acid ethyl ester ((CH₃)₂N–CH₂–CH(OH)–CH₂–CO–OC₂H₅) | 91 | 93 |
| 13 | 3-hydroxybutanethioic acid S-ethyl ester (OH–CH(CH₃)–CH₂–CO–SC₂H₅) | 87 | 65 |
| 14 | 2-(ethoxycarbonyl)cyclohexan-1-ol | 90 | see Table 3 |

TABLE 2-continued

| Example No. | Product | Yield (%) | Optical Yield (% ee) |
|---|---|---|---|
| 15 | 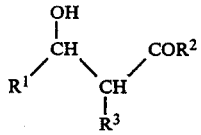 | 85 | see Table 3 |
| 16 | Cl—CH₂—CH(OH)—CH₂—C(O)OCH₃ | 90 | 67 |
| 17 | Br—CH₂—CH(OH)—CH₂—C(O)OCH₃ | 95 | 45 |

TABLE 3

| Example No. | Syn:Anti Ratio | Optical Yield (% ee) Syn | Optical Yield (% ee) Anti |
|---|---|---|---|
| 7 | 60:40 | 92 | 88 |
| 8 | 50:50 | 90 | 87 |
| 14 | 55:45 | 91 | 89 |
| 15 | 60:40 | 92 | 86 |

As described above, the present invention provides an industrially valuable process for preparing a useful optically active alcohol at high efficiency.

While the invention has been described in detail and with reference to specific embodiments thereof, it will be apparent to one skilled in the art that various changes and modifications can be made therein without departing from the spirit and scope thereof.

What is claimed is:

1. A process for preparing an optically active alcohol represented by the formula (I):

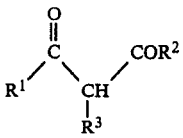

(I)

wherein R¹ represents an alkyl group containing from 1 to 8 carbon atoms; a lower alkyl group substituted with a halogen atom, a hydroxyl group, a benzyloxy group, or a lower alkoxy group; a trifluoromethyl group; a phenyl group; or a benzyl group; R² represents OR⁴, wherein R⁴ represents an alkyl group having from 1 to 8 carbon atoms, SR⁵, wherein R⁵ represents a lower alkyl group or a phenyl group, or NR⁶R⁷, wherein R⁶ and R⁷, which may be the same or different, each represents a hydrogen atom, a lower alkyl group or a benzyl group; and R³ represents a hydrogen atom, a halogen atom, a lower alkyl group, a lower alkoxycarbonyl group or a lower alkoxycarbonyl-lower alkyl group; or R¹ and R³ are connected to each other to form a methylene chain, forming a 4- to 6-membered ring together with the carbon atoms therebetween, which comprises asymmetrically hydrogenating a β-keto acid derivative represented by formula (II):

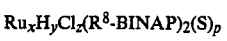

(II)

wherein R¹, R², and R³ are as defined above, in the presence of a ruthenium-optically active phosphine complex as a catalyst.

2. A process as claimed in claim 1, wherein said ruthenium-optically active phosphine complex is a compound represented by formula (III):

$$Ru_xH_yCl_z(R^8\text{-BINAP})_2(S)_p$$ (III)

wherein R⁸-BINAP represents a tertiary phosphine represented by formula (IV):

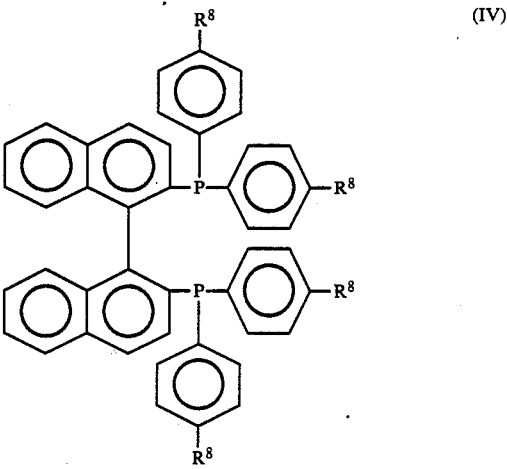

(IV)

wherein R⁸ represents a hydrogen atom, a methyl group or a t-butyl group; S represents a tertiary amine; when y represents 0, then x represents 2, z represents 4, and p represents 1; and when y represents 1, then x represents 1, z represents 1, and p represents 0, or a compound represented by formula (V):

(V)

wherein R⁸-BINAP is as defined above; Y represents ClO₄, BF₄ or PF₆; when l represents 0, then v represents 1, and w represents 2; and when l represents 1, then v represents 2, and w represents 1.

* * * * *